United States Patent [19]
Benach

[11] Patent Number: 6,101,418
[45] Date of Patent: Aug. 8, 2000

[54] DEVICES FOR ELECTROTHERAPY

[75] Inventor: Jose Calbet Benach, Barcelona, Spain

[73] Assignee: Indiba, S.A., Barcelona, Spain

[21] Appl. No.: 09/121,013

[22] Filed: Jul. 22, 1998

[30] Foreign Application Priority Data

Jul. 24, 1997 [ES] Spain .................................. 9701641

[51] Int. Cl.$^7$ .................................................. A61N 1/04
[52] U.S. Cl. ................................................ 607/65; 607/63
[58] Field of Search ................................ 607/65, 66, 67, 607/63, 76

[56] References Cited

U.S. PATENT DOCUMENTS 1,681,708  8/1928  Murakoshi .
2,622,601  12/1952  Nemec .
3,338,240  8/1967  Raupp .

FOREIGN PATENT DOCUMENTS 549883  12/1985  Spain .
2102301  7/1997  Spain .

*Primary Examiner*—Scott M. Getzow
*Attorney, Agent, or Firm*—Steinberg & Raskin, P.C.

[57] ABSTRACT

With these devices a relative H F (high frequency) electric current applicable to the human body is generated by means of an active electrode and a neutral or return electrode, whose electrodes are connected to the transformer of the output stage of the corresponding circuit. The invention is characterised by the coil of the output transformer having on the secondary winding, besides connections for the end terminals for connecting the neutral or return electrode and an active metallic electrode with electrically insulating cover, an intermediate terminal for connecting an active metallic electrode without insulating cover, whose terminal is furnished with an adequate very reduced impedance with an average which adapts only and exclusively to the different sizes of said metallic electrodes without metallic cover which are used.

2 Claims, 1 Drawing Sheet

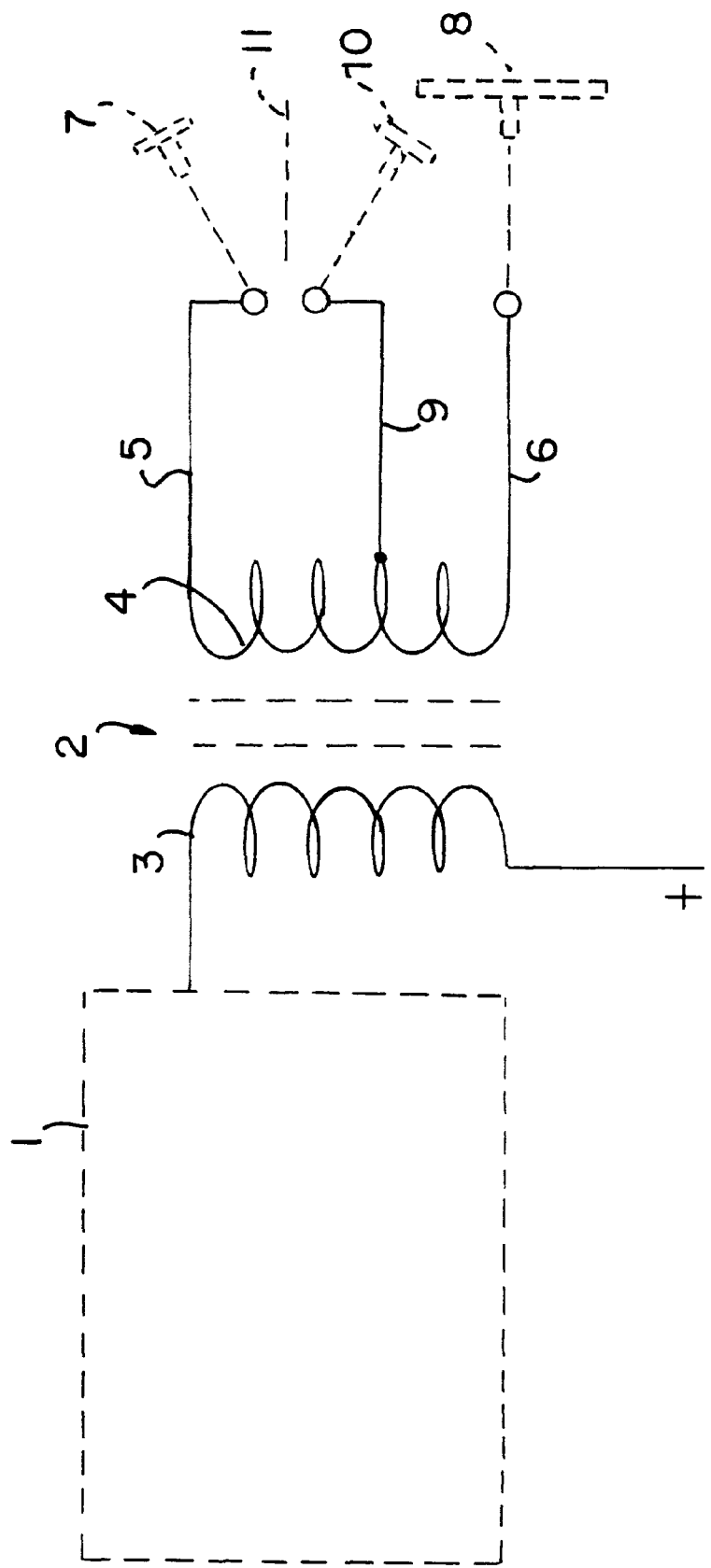

DEVICES FOR ELECTROTHERAPY

FIELD OF THE INVENTION

The present invention relates to a device for electrotherapy, mainly adapted for to the treatment of parts of the body affected by neoplasias and other phenomena originated by abnormal cell growth.

BACKGROUND OF THE INVENTION

In the present state of the art devices for electrotherapy are known which are based on the application of high frequency currents aimed at producing hyperthermia effects, i.e., local heating of the cell tissues of determined parts of the body, affected by neoplasias and analogous ailments.

A pair of symmetrical and metallic plates are used in one of the known hyperthermia devices for electrotherapy, acting the body of the patient as a resistor element, whose plates or electrodes are generally connected to the transformer of the output stage of the corresponding circuit.

This type of device has been improved by the subject matter of Patent ES-2102301 (P9400929), held by the common assignee of the present application which discloses an active metallic electrode which shows a more reduced dimension than the return electrode also constituted by a metallic plate, the dimensional difference between the two electrodes, arranged one in front of the other on the two sides of the body region to be treated, determines an effect of increased impedance that, combined with the frequency potency amplifier generator, with adequate output impedance, determines the necessary increase in the treatment temperature at the local level.

In these devices, given their functioning characteristics and the nature of their operation, usually, in the known types of oscillation generators for electrotherapy, the working potency must be reduced to a minimum when applying the electrode to the pertinent body area and when separating the electrode itself at the end of the treatment operation. Sparks and/or burns on the treated areas can also be caused by the known devices for electrotherapy.

OBJECTS AND SUMMARY OF THE INVENTION

In order to avoid these inconveniences and provide safety and comfort in the use of the device, this invention is characterized by the fact that the coil of the output transformer present at the secondary winding, besides the end terminals for connecting the neutral or return electrode and a metallic active electrode with an electrically insulating cover (according to Patent ES-549.883, held by the common assignee of the present application, an intermediate terminal for connecting an active metallic electrode without insulating cover, whose terminal is furnished with an adequate, very reduced impedance with an average which adapts only and exclusively to the different sizes of said metallic electrodes without insulating cover used, thus sparks are eliminated when setting and withdrawing these electrodes during their application to the body of the patient and thus avoiding the chances of causing burns to the same.

BRIEF DESCRIPTION OF THE DRAWING

These and other characteristics will be better understood in the detailed description which follows. A drawing sheet is attached to facilitate its understanding which represents a practical application case which is mentioned only as an example not limiting the scope of the present invention.

In the drawings, a only FIGURE is the schematic representation of the output stage corresponding to the circuit of this improved device.

DETAILED DESCRIPTION OF THE PREFERRED EMBODIMENTS

In accordance with the drawings, reference 1 indicates the frequency amplifier, corresponding to the output stage or the end of the circuit, to which the HF (High frequency) transformer 2 is connected, being 3 the primary winding of the coil of said transformer and comprising the secondary winding 4 of the same, at its ends, two terminals 5 and 6 to which the active metallic electrode -7- with electrically insulating cover and the neutral or return electrode 8 are respectively connected. At an intermediate point of the secondary winding 4 of the coil, there is another terminal 9 destined to the connection of an active metallic electrode 10 without insulating cover, whose terminal is furnished with an adequate very low impedance with an average-which adapts only and exclusively to the different sizes of said electrodes 10 which are used in the treatment of the patient. Reference 11 indicates the medium point of the application output, The intermediate terminal 9 has a very low impedance, i.e. resistance value, of about 50 ohms. This value was obtained by measuring the resistance values exhibited by various parts of human body and then taking an average of these values. By selecting a terminal having a very low impedance for the intermediate terminal 9, the device according to the present invention eliminates the generation of sparks during the application and removal of the terminals (electrodes) from the body. The configuration described above has enabled the device according to the present invention to deliver considerably more current without generation of sparks or the unwanted burning of tissue. Conventional devices can generate sparks at as low as 50 W whereas the device according to the present invention is capable of delivering 200 W without spark generation.

What is claimed is:

1. An electrotherapy device comprising:
   a frequency amplifier;
   a transformer operable connected to said frequency amplifier, said transformer having a primary coil and a secondary coil, said secondary coil having a first end and a second end and a plurality of coils interposed between said first and second ends;
   an active electrode having a electrically insulating cover operably connected to said first end;
   a neutral return electrode operably connected to said second end; and
   an intermediate terminal operably connected to one of said plurality of coils interposed between said first and second ends, said intermediate terminal having a selected low impedance value for eliminating sparks during an application and a removal of said electrodes to and from a patient's body.

2. The device according to claim 1, wherein said selected low impedance value is about 50 ohms.

* * * * *